United States Patent
Dhatt et al.

(10) Patent No.: US 12,016,731 B2
(45) Date of Patent: Jun. 25, 2024

(54) ULTRASOUND CREDENTIALING SYSTEM

(71) Applicants: FUJIFILM SONOSITE, INC., Bothell, WA (US); FUJIFILM CORPORATION, Tokyo (JP)

(72) Inventors: Davin Dhatt, Woodinville, WA (US); Paul Danset, Kirkland, WA (US); Thomas Duffy, Stanwood, WA (US); Hidetoshi Takayama, Kaiseimachi (JP); Tomoki Inoue, Kaiseimachi (JP); Tsuyoshi Matsumoto, Kaiseimachi (JP)

(73) Assignee: FUJIFILM SONOSITE, INC., Bothell, WA (US)

( * ) Notice: Subject to any disclaimer, the term of this patent is extended or adjusted under 35 U.S.C. 154(b) by 17 days.

(21) Appl. No.: 18/047,346

(22) Filed: Oct. 18, 2022

(65) Prior Publication Data
US 2024/0122579 A1    Apr. 18, 2024

(51) Int. Cl.
*A61B 8/00* (2006.01)
*A61B 8/08* (2006.01)

(52) U.S. Cl.
CPC .......... *A61B 8/5292* (2013.01); *A61B 8/4254* (2013.01); *A61B 8/429* (2013.01); *A61B 8/467* (2013.01); *A61B 8/58* (2013.01)

(58) Field of Classification Search
CPC .................................................. A61B 8/4254
See application file for complete search history.

(56) References Cited

U.S. PATENT DOCUMENTS

| | | | |
|---|---|---|---|
| 2015/0327841 A1* | 11/2015 | Banjanin ............. | A61B 8/4263 600/443 |
| 2017/0303899 A1* | 10/2017 | Willsie ................. | A61B 8/461 |
| 2017/0352294 A1* | 12/2017 | Nataneli ............... | A61B 5/066 |
| 2018/0242946 A1* | 8/2018 | Grbic .................... | A61B 8/58 |
| 2019/0365346 A1* | 12/2019 | Elliot ................... | A61B 8/0875 |
| 2021/0366106 A1* | 11/2021 | Yao ....................... | G16H 50/70 |
| 2022/0202393 A1* | 6/2022 | Wang .................. | A61B 8/4209 |
| 2023/0200778 A1* | 6/2023 | Venkataramani ..... | A61B 8/463 600/437 |

FOREIGN PATENT DOCUMENTS

DE   102016204368 A1 * 9/2017
WO   WO-2022096471 A1 * 5/2022

* cited by examiner

*Primary Examiner* — Patrick Fernandes
*Assistant Examiner* — Aminah Asghar
(74) *Attorney, Agent, or Firm* — Womble Bond Dickinson (US) LLP

(57) ABSTRACT

Systems and methods for automated ultrasound credentialing are described. In some embodiments, a credentialing system for issuing a sonographer credential to a sonography candidate includes an ultrasound probe coupled to a computing device and configured to generate ultrasound data. The computing device is configured to generate, based on the ultrasound data and as part of an automated review, an ultrasound examination score. The computing device is configured to transfer, based on the ultrasound examination score, the sonography candidate from the automated review to a manual review by a reviewer.

18 Claims, 12 Drawing Sheets

ULTRASOUND CREDENTIALING SYSTEM

Embodiments disclosed herein relate to ultrasound systems. More specifically, embodiments disclosed herein relate to ultrasound credentialing systems.

BACKGROUND

Generally, ultrasound systems generate ultrasound images by transmitting sound waves at frequencies above the audible spectrum into a body, receiving echo signals caused by the sound waves reflecting from internal body parts, and converting the echo signals into electrical signals for image generation. Because they are non-invasive and can provide immediate imaging results, ultrasound systems are used ubiquitously in care facilities. In most of these care facilities, the demand for credentialed ultrasound operators far exceeds the number of available credentialed ultrasound operators.

This disparity in demand and supply of credentialed ultrasound operators is in part due to the extensive training and review processes of credentialing systems used by the care facilities to credential an ultrasound operator. For instance, candidates (e.g., students) who are training to be credentialed ultrasound operators are often required to conduct ultrasound examinations on a variety of patients with a variety of medical conditions, and submit their ultrasound data (e.g., imaging results) for manual review and approval by a reviewer at the care facility. This review process is generally not capable of providing real-time feedback to the candidate during the ultrasound examination, as the reviewer is generally not available to review ultrasound data for each candidate during the ultrasound examination. This issue is exacerbated when multiple candidates are simultaneously generating ultrasound examination data for review, e.g., based on different patients in a care facility. Accordingly, the candidate may not receive feedback from the reviewer until significantly after the ultrasound examination, such as days or weeks. Therefore, the ultrasound examination may not be fresh in the candidate's mind when the candidate receives the reviewer feedback, so that the candidate may not take full advantage of the feedback, slowing the credentialing process for the candidate.

The conventional credentialing system is necessarily subjective as it relies on human judgement, and is often inaccurate, since a reviewer may judge ultrasound data as acceptable when it is unacceptable, or vice versa. Moreover, the conventional credentialing system generally lacks a standardization among reviewers (within a care facility and/or across different care facilities), so that one reviewer may judge ultrasound data as unacceptable, and another reviewer may judge the same ultrasound data as acceptable. Also, the reliance on the reviewer (e.g., one or more senior clinicians) places a significant resource burden on the care facility in terms of the reviewers' time to review submissions by candidates, and to generally oversee the credentialing program.

Furthermore, for ultrasound examinations that require urgent care (e.g., the determination of free fluid in a patient), candidates may not be able to submit ultrasound data for review based on examination of a live patient. In these cases, the credentialing system can generate a mock ultrasound image via a training or simulator system, and the candidate can submit the mock ultrasound image to a reviewer of the credentialing system. The reviewer, however, usually has an inherent bias when grading the mock ultrasound image, as the reviewer is aware that the mock ultrasound image is not a true ultrasound image. Hence, the reviewer may be likely to grade the mock ultrasound image as acceptable because it is a mock image and not a true ultrasound image.

Accordingly, conventional ultrasound credentialing systems can introduce delays in the credentialing process, burden the care facility, and result in poorly trained, but still credentialed, ultrasound operators. Hence, patients requiring an ultrasound examination may receive less than the best care available.

SUMMARY

Systems and methods for automated ultrasound credentialing are described. In some embodiments, a credentialing system for issuing a sonographer credential to a sonography candidate includes a computing device and an ultrasound probe coupled to the computing device and configured to generate ultrasound data. The computing device is configured to generate an ultrasound examination score based on the ultrasound data and as part of an automated review. The computing device is configured to transfer, based on the ultrasound examination score, the sonography candidate from the automated review to a manual review by a reviewer.

In some embodiments, a credentialing system for issuing a sonographer credential to a sonography candidate includes an ultrasound system configured to generate ultrasound images. The credentialing system includes a candidate credentialing application implemented at least partially in hardware of the credentialing system and configured to generate image quality scores for a first subset of the ultrasound images and communicate, based on the image quality scores, a second subset of the ultrasound images to a reviewer computing device.

In some embodiments, a sonography credentialing system includes an ultrasound probe configured to generate ultrasound data. The sonography credentialing system includes a computing device configured to generate an ultrasound image based on the ultrasound data. The sonography credentialing system includes a neural network implemented at least partially in hardware of the computing device to generate an image quality score based on the ultrasound image. The sonography credentialing system includes a credentialing device configured to issue a sonographer credential based on the image quality score.

In some embodiments, a method implemented by a computing device includes receiving, from an ultrasound probe coupled to the computing device, ultrasound data. The method includes generating, with the computing device, an image quality score based on the ultrasound data. The method includes communicating, based on the image quality score, the ultrasound data to a reviewer computing device for user credentialing.

In some embodiments, a method implemented by a computing device includes receiving, from an ultrasound probe coupled to the computing device, ultrasound data. The method includes generating, with the computing device, an image quality score based on the ultrasound data. The method includes halting, based on the image quality score, communication of the ultrasound data to a reviewer computing device for user credentialing.

In some embodiments, a method implemented by a computing device includes receiving, from an ultrasound probe coupled to the computing device, ultrasound data. The method includes generating, with the computing device, an image quality score based on the ultrasound data. The method includes communicating the image quality score and the ultrasound data to a credentialing server for user credentialing.

In some embodiments, a method implemented by a computing device includes receiving ultrasound images. The method includes generating image quality scores for a first subset of the ultrasound images. The method includes communicating, based on the image quality scores, a second subset of the ultrasound images to a reviewer computing device for user credentialing.

In some embodiments, a method implemented by a computing device includes receiving ultrasound images. The method includes generating, with a neural network implemented at least partially in hardware of the computing device, image quality scores for the ultrasound images. The method includes issuing, based on the image quality scores, a sonography credential.

Other systems, machines, and methods for ultrasound credentialing are also described.

BRIEF DESCRIPTION OF THE DRAWINGS

The appended drawings illustrate examples and are, therefore, exemplary embodiments and not considered to be limiting in scope.

DETAILED DESCRIPTION

Figure 1:
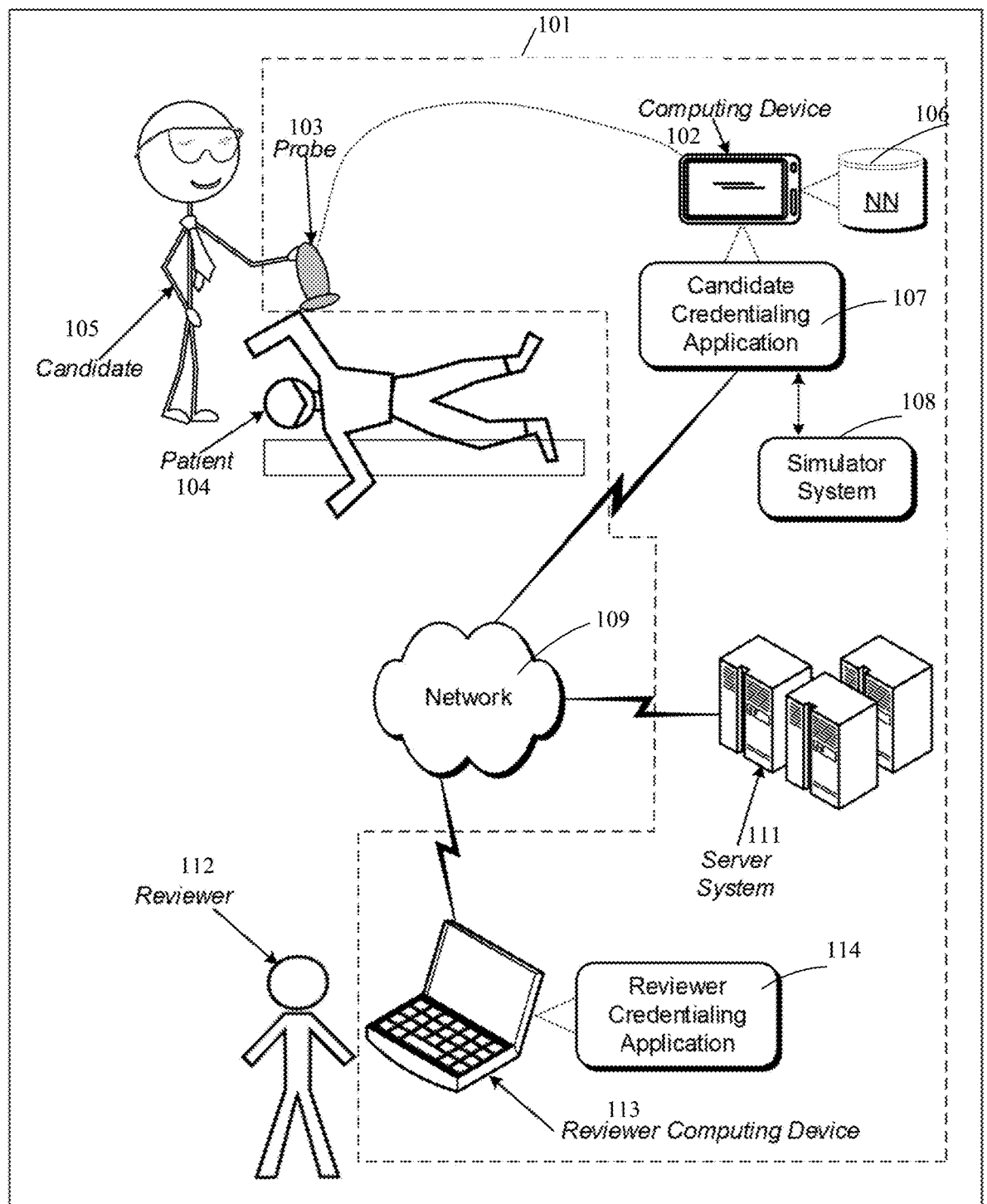
FIG. 1 is a view illustrating an environment for implementing a credentialing system according to some embodiments.

Systems and methods for automated ultrasound credentialing are described. In some embodiments, a credentialing system for issuing a sonographer credential to a sonography candidate includes a computing device and an ultrasound probe coupled to the computing device and configured to generate ultrasound data. The computing device is configured to generate, based on the ultrasound data and as part of an automated review, an ultrasound examination score. The computing device is configured to transfer, based on the ultrasound examination score, the sonography candidate from the automated review to a manual review by a reviewer.

Conventional ultrasound credentialing systems can introduce delays in the credentialing process, place resource burdens on care facilities, and result in poorly trained, but still credentialed, ultrasound operators, so that patients requiring an ultrasound examination may receive less than the best care available.

Embodiments of the systems, devices, and methods for ultrasound credentialing disclosed herein constitute numerous advantages over conventional credentialing systems. The embodiments disclosed herein remove biases and improve the speed of credentialing comparing to conventional ultrasound credentialing systems. The embodiments disclosed herein facilitate real-time feedback to a candidate during an ultrasound examination, allowing the candidate to immediately incorporate the feedback into the ultrasound exam without delay, while the examination is fresh in the candidate's mind. This immediacy is not possible with conventional credentialing systems that rely on feedback from a manual reviewer. The embodiments for ultrasound credentialing disclosed herein are objective and unbiased in reviewing and grading ultrasound data submitted by candidates for credentialing. In contrast, because conventional credentialing systems can rely exclusively on manual reviews, they are necessarily subjective and biased. The embodiments disclosed herein facilitate a credentialing process that can be standardized within a care facility, and across different care facilities. In contrast, conventional credentialing systems are usually ad-hoc and not standardized across care facilities. The embodiments disclosed herein reduce the burden of resources in the care facility, such as the time demand on reviewers (e.g., trained clinicians), compared to conventional credentialing systems.

Reference in the specification to "one embodiment", "an embodiment", "one example", or "an example" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described may be performed in a different order. Moreover, some operations may be performed in parallel rather than sequentially.

In the specification, the term "and/or" describes three relationships between objects that may exist. For example, A and/or B may represent the following cases: only A exists, both A and B exist, and only B exist, where A and B may be singular or plural.

FIG. 1 is a view 100 illustrating an environment for implementing a credentialing system 101 according to some embodiments. The credentialing system includes an ultrasound system which can be operated by a candidate 105 (e.g., a student who is training to become a credentialed ultrasound operator). The ultrasound system 101 includes a probe 103 and a computing device 102 coupled to the probe via a communication link. The communication link between the probe and the computing device can be wired, wireless, or a combination thereof. The computing device 102 can include any suitable computing device, such as a tablet, smart phone, heads-up display, goggles, glasses, ultrasound machine, or combinations thereof. As shown in FIG. 1, the computing device 102 can include one or more neural networks (NN) 106 that can be implemented at least partially in hardware of the computing device. The computing device 102 also includes a candidate credentialing application 107 that can be implemented by a processor of the computing device (not shown in FIG. 1). For example, a memory of the computing device can store instructions that when executed by the processor cause the computing device to implement the candidate credentialing application. As shown in FIG. 1, the candidate credentialing application 107 is coupled to a simulator system 108. In some embodiments, the simulator system 108 includes a dummy patient, and the ultrasound probe transmits ultrasound into the dummy patient and generates ultrasound data based on reflections of the ultrasound from the dummy patient, as described in further detail below.

As shown in FIG. 1, the ultrasound system 101 is coupled to a network 109 (e.g., a computing network). In some embodiments, one or more of the probe 103 and the computing device 102 are coupled to the network 109 to couple the ultrasound system to the network. In an example, the network includes a care facility network, such as a secured Wi-Fi network operated by a care facility (e.g., hospital). The credentialing system can include a server system 111 coupled to the network 109, so that the server system is in communication with the computing device 102 operated by the candidate. The server system 111 can include a credentialing database to archive data related to the credentialing of a candidate, such as examination results, reviewer feedback, ultrasound data, metadata regarding the ultrasound data, etc. In an example, the server system includes a database of neural networks, and the computing device 102 operated by the candidate can include one or more neural networks supplied by the server system. For example, the neural network(s) 106 can include one or more neural networks received from the server system 111. In some embodiments, the credentialing application 107 determines an examination type being performed by the candidate, and the server system retrieves a suitable neural network for the examination type and provides the neural network to the credentialing application for implementation on the candidate's computing device. In some embodiments, the candidate's computing device includes multiple computing devices. In some embodiments, the candidate's computing device includes the server system, and a neural network that is implemented "in the cloud" by a server. Alternatively, the server system can be separate from the candidate's computing device, such as a server system maintained by the care facility.

The credentialing system can also include a reviewer computing device 113 operated by a reviewer 112, e.g., a trained and credentialed sonographer who manually reviews and grades ultrasound data submitted by the candidate 105 as part of the credentialing process for the candidate. The reviewer computing device 113 can include a reviewer credentialing application 114 that can be implemented by a processor of the reviewer computing device (not shown in FIG. 1). For example, a memory of the reviewer computing device can store instructions that when executed by the processor cause the reviewer computing device to implement the reviewer credentialing application. The reviewer can, via a user interface of the reviewer credentialing application, perform any suitable function as part of the credentialing review, such as review ultrasound data supplied by a candidate, provide feedback (e.g., comments, a grade, etc.) back to the candidate, and archive data on the server system.

During an ultrasound examination on a patient 104, the sonography candidate 105 can use the ultrasound system 101 (e.g., the probe 103 and the computing device 102) to generate ultrasound data for credentialing with the credentialing system. In an example, unlike conventional credentialing systems, the credentialing system does not necessarily send the ultrasound data to the reviewer for manual review, but instead implements one or more neural networks 106, such as on the candidate's computing device 102, to automatically determine a property of the ultrasound data and provide feedback based on the property in real time, during the ultrasound examination, to the candidate 105. Feedback generated by the neural network can also be communicated by the computing device 102 to the server system 111 for archiving as part of the credentialing.

The neural network 106 can generate any suitable output based on the ultrasound data. In some embodiments, the credentialing system implements the neural network to generate a quality measure of an ultrasound image, such as a number between zero and one, with zero indicating poor quality and one indicating excellent quality, or a binary label, such as "pass" or "fail". In some embodiments, the binary label is generated by applying a threshold to a probability of a measure generated by the neural network, such as a probability that an ultrasound image includes an acceptable view. In some embodiments, the threshold is an image quality threshold, or other measure threshold. In some embodiments, the image quality measure indicates that the image has a sufficient quality to perform a predetermined action. In some embodiments, the neural network is trained to generate the binary label directly (e.g., without first generating a probability and applying a threshold to it), by suitable choice of the loss function used to train the neural network. The candidate credentialing application 107 can display, via a user interface of the computing device 102, the quality measure to the candidate. Additionally or alternatively, the candidate credentialing application 107 can generate a grade based on the quality of the ultrasound image, such as by assigning a letter grade A, B, C, D, or F based on the quality measure generated by the neural network 106. The grade can be an indication of the usability of the ultrasound data, such as whether or not an ultrasound image generated from the ultrasound data is "good enough" to determine a pneumothorax condition.

The neural network 106 can receive any suitable inputs to generate a quality measure and/or grade for a candidate. As discussed above, the neural network can receive one or more ultrasound images produced during an ultrasound examination by a candidate 105. Additionally, the neural network can include one or more secondary (e.g., additional) inputs to generate a quality measure and/or grade for a candidate, as described in further detail with respect to FIG. 3.

In some embodiments, the ultrasound probe 103 includes an inertial measurement unit (IMU) that can measure one or more of force, acceleration, angular rate, and magnetic field. An IMU can include a combination of accelerometers, gyroscopes, and magnetometers, and generate location and/or orientation data including data representing six degrees of freedom, such as yaw, pitch, and roll angles in a coordinate system. Additionally or alternatively, the ultrasound system can include a camera to determine location and/or orientation data for the ultrasound probe. The location and/or orientation data can indicate probe movement. The neural network can process the location and/or orientation data as a secondary input that is in addition to the ultrasound image(s).

In some embodiments, the neural network also receives as a secondary input an indication of a behavior of the candidate during the examination. For example, a poor or untrained ultrasound operator may move the probe more than a skilled or trained operator during the ultrasound examination, which may cause discomfort to the patient. Accordingly, an example of a secondary input that indicates a behavior of the candidate includes motion data of the candidate. For example, the candidate can wear motion sensors on their clothing that determines motion data of the candidate (e.g., a degree of movement of the candidate's arm) during an examination. For another example, the probe includes one or more motion sensors (e.g., IMU, gyro, location/orientation sensor, movement sensor, or other motion sensor) to collect motion data of the candidate. Additionally or alternatively, a camera in the examination room can generate the motion data. In an example, a secondary input to the neural network includes an amount of time, such as the time it takes a candidate to generate and save an ultrasound image for review, starting from when the candidate starts acquiring ultrasound images using the probe/ultrasound system. For instance, a "poor" operator may take a lot of time moving the probe to the proper place where the proper ultrasound image is obtained, and this excessive time can have a negative psychological impact in the patient.

Figure 2:
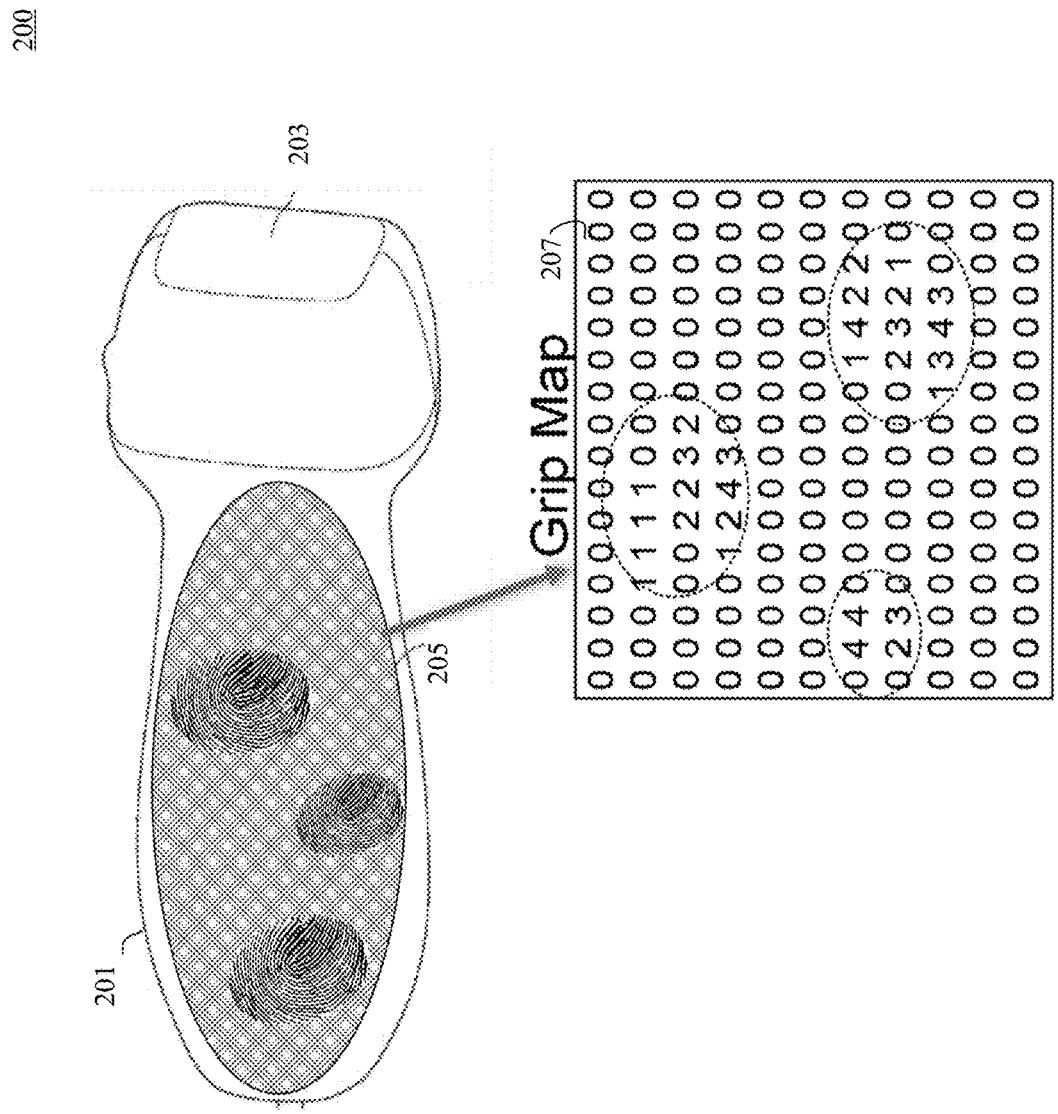
FIG. 2 is a view illustrating an ultrasound probe with a sensor region to determine a grip orientation according to some embodiments.

Additionally or alternatively, a secondary input indicative of candidate behavior can include audio content, including audio content spoken by the candidate, the patient, and/or another person viewing the examination. For instance, the audio content can include a conversation between the candidate and the patient, so that the neural network can be trained to generate a better score for a candidate when they communicate with a patient in a positive way, such as by telling the patient what to expect next during the examination. In an example, the patient says "you're hurting me", or someone in the room tells the candidate to move the probe in a certain way (e.g., the candidate got help to get an appropriate view). FIG. 2 is a view 200 illustrating an ultrasound probe 201 with a sensor region 205 to determine a grip orientation according to some embodiments. In some embodiments, ultrasound probe 201 represents ultrasound probe 103, or another ultrasound probe. In some embodiments, ultrasound probe 201 represents an ultrasound probe with a sensor region to determine a grip orientation as described in U.S. patent application Ser. No. 18/045,477, entitled "CONFIGURING ULTRASOUND SYSTEMS BASED ON SCANNER GRIP", filed on Oct. 11, 2022 that is incorporated herein by reference in its entirety. As shown in FIG. 2, the ultrasound probe 201 includes a sensor region 205 to detect a grip orientation and a transducer coupled to a lens 203. In FIG. 2, the sensor region 205 is shown as an ellipsoid. However, the sensor region 205 can be of any suitable shape. In some embodiments, the sensor region 205 substantially covers the surface of the ultrasound probe 201, e.g., the sensor region can cover substantially all of the ultrasound probe 201, including or excluding the lens 203. In some embodiments, the sensor region 205 covers an area that a user usually grips (e.g., a hand grip portion of the probe that is narrower than a transducer head portion of the probe).

In some embodiments, the transducer of the ultrasound probe 201 includes an ultrasound transducer array and electronics coupled to the ultrasound transducer array to transmit ultrasound signals to a patient's anatomy and receive ultrasound signals reflected from the patient's anatomy. The ultrasound probe 201 can include in, on, or under the sensor region 205 any suitable type of sensors for determining a grip orientation. In some embodiments, the ultrasound probe 201 includes capacitive sensors that can measure a capacitance, or change in capacitance, caused by a user's touch or proximity of touch, as is common in touchscreen technologies. Additionally or alternatively, the ultrasound probe 201 can include pressure sensors configured to determine an amount of pressure caused by the user's grip on the probe.

In some embodiments, the ultrasound system receives the sensor data from sensors of the sensor region 205 and generates a grip map 207 representing the sensor data. As shown in FIG. 2, the grip map 207 includes the sensor data in a two-dimensional (2D) grid (e.g., a matrix). A node of the grid can correspond to a sensor of the sensor region 205, and include the sensor data from the sensor. As an example, each intersection of the cross hatching illustrated in the sensor region 205 of FIG. 2 can correspond to a sensor for determining a grip orientation, and hence a node in the 2D grid. The sensor data can include a multi-level indicator that indicates an amount of pressure on the sensor, such as an integer scale from zero to five. For example, a "0" can indicate that no pressure from the user's hand is detected at the sensor, and a "1" can indicate a small amount of pressure from the user's hand is detected at the sensor. A "2" can indicate a larger amount of pressure from the user's hand is detected at the sensor than a "1", and a "5" can indicate a maximum amount of pressure from the user's hand is detected at the sensor. The neural network (e.g., the NN 106 in FIG. 1) can receive the grip orientation, such as grip map 207, as a secondary input that is in addition to an ultrasound image to generate a quality measure and/or grade for a candidate. Other examples of secondary inputs include pressure data (e.g., how much pressure is applied from the probe to the patient), temporal data (e.g., how long it takes a candidate to operate the ultrasound system to perform an ultrasound examination), and the like.

Figure 3:
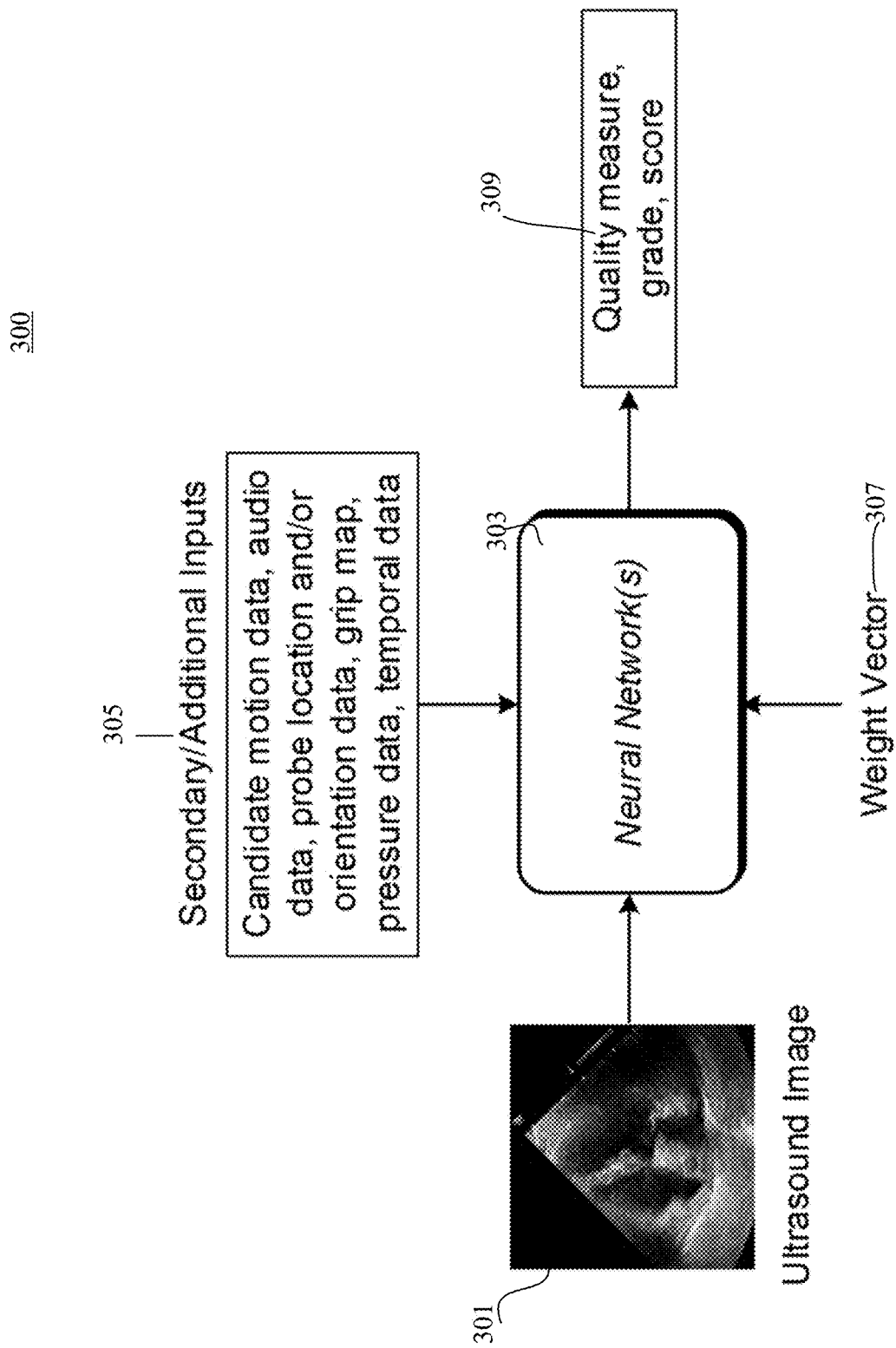
FIG. 3 is a view illustrating a system to generate data related to the evaluation of the candidate based on one or more ultrasound images and one or more secondary inputs according to come embodiments.

FIG. 3 is a view 300 illustrating a system to generate data related to the evaluation of the candidate based on one or more ultrasound images and one or more secondary inputs according to some embodiments. As shown in FIG. 3, a neural network 303 receives an ultrasound image 301 as a primary input, and one or more secondary inputs 305, as discussed above, to generate an output 309. The neural network 303 is an example of the neural network 106 on FIG. 1. In some embodiments, the output 309 includes data related to the evaluation of the candidate, e.g., a quality measure, a grade, and/or a score for a candidate during the ultrasound examination. The neural network 303 can combine the ultrasound image 301 with one or more secondary inputs 305 in any suitable way. In some embodiments, the neural network concatenates the secondary input and the ultrasound image, and processes the concatenated data at the top (first) layer of the neural network. In some embodiments, the neural network processes the ultrasound image with one or more layers of the neural network and concatenates the results (e.g., a feature map based on the ultrasound image) with the secondary input for subsequent layers of the neural network.

In some embodiments, neural network 303 includes a plurality of networks and/or sections. Each section can include one or more neural networks. In some embodiments, the neural network processes the ultrasound image using two sections, with the second section receiving a secondary input. The neural network 303 can combine one or more of the results output from the first and second sections with one or more of the ultrasound image and the secondary input. In some embodiments, one or more ultrasound images 301 are input to a first neural network and an output of the first neural network (e.g., a feature map, or other output) is combined with one or more secondary inputs 305 to input to a second neural network to generate output 309. In some embodiments, one or more secondary inputs 305 are input to a first neural network and an output of the first neural network is combined with one or more ultrasound images 301 to input to a second neural network to generate output 309.

In some embodiments, the neural network 303 receives a weight vector that assigns relative weights to the secondary inputs 305. For example, the weight vector can include user-assigned values between zero and one to place more or less emphasis on the secondary inputs, e.g., by weighting probe orientation data more heavily than audio data. By allowing the weight to include user-assigned weights, the credentialing system can be adjusted over time to align with current trends in sonography examinations. For example, today, the current state of the art may place significant emphasis on temporal data (e.g., how long a candidate takes to perform an ultrasound examination). In the future, the current state of the art may change and place more emphasis on pressure data. The credentialing system can easily accommodate these changes via the weight vector. In some embodiments, the credentialing system credentials a candidate based on a combination of automated reviews with neural networks 303 and manual reviews performed by the reviewer (e.g., reviewer 112 in FIG. 1). For instance, the credentialing system can restrict the review of ultrasound data to the automated review of the ultrasound data using the candidate credentialing application and the neural networks as discussed above until a threshold of performance is met. Once the performance threshold is satisfied, the credentialing system can provide ultrasound data from the candidate to the reviewer for reviewing as part of a manual review.

An example of the performance threshold includes that the candidate receives a passing score (e.g., a binary "pass" label or a letter grade of A or B) on a prescribed number of examinations, such as the five most recent examinations. Additionally or alternatively, the performance threshold can require a type of examination be passed (e.g., receive an acceptable letter grade), such as for a bladder scan or a scan according to an ultrasound protocol. An example of an ultrasound protocol is Extended Focused Assessment with Sonography in Trauma (eFAST) that is designed to detect peritoneal fluid, pericardial fluid, pneumothorax, and/or hemothorax in a trauma patient. In an example, for the blood vessel echo examination of the lower extremities to diagnose the presence or absence of deep vein thrombosis (DVT), the credential system can evaluate whether several reference cross sections are sequentially observed from the central side to the peripheral side. In another example, for the examination of the abdomen, when the order of observing a plurality of representative sites is predetermined for each hospital, the credential system can evaluate whether the examination is performed in accordance with the predetermined order. Hence, the credentialing system can transfer the candidate from automated review to manual review based on a history of examinations performed by the candidate.

In some embodiments, to credential a candidate, the credentialing system imposes a number of review iterations, with each iteration including first automated reviews with neural networks, then followed by manual reviews by the reviewer upon successful completion of the automated reviews. In some embodiments, the credentialing system groups the iterations of the review process based on one or more characteristics, e.g., by difficulty, content, patient availability, and other characteristics. For example, a first iteration can include ultrasound examinations of a bladder, a second iteration can include ultrasound examinations according to ultrasound protocols, a third iteration can include ultrasound examinations of cardiac anatomy, a fourth can include ultrasound examinations using a simulator system (e.g., the simulator system 108) (discussed below in more detail), and the like.

In some embodiments, the credentialing system includes a credentialing database that stores examination results and examination data of sonography candidates. For instance, the credentialing database can store data used as inputs to a neural network and data generated by the neural network as illustrated in FIG. 3, such as ultrasound images, sensor data, motion data, orientation data, audio spoken by a candidate and/or a patient, a grip map, examination score, image quality score, etc. The server system 111 in FIG. 1 can include the credentialing database. Data stored in the credentialing database can be provided as input to a neural network. Hence, the neural network can generate an examination score for a sonography candidate based not only on data from a current examination performed by the candidate, but also past examinations performed by the candidate. The credentialing system can be configured to weight previous examinations differently than a current examination, such as by using more difficult thresholds (such as a higher score threshold) for a current examination and easier thresholds for previous examinations. In an example, the data from the credentialing database is provided to a decision tree that deterministically generates an examination score based on a history of data for the sonography candidate. Additionally or alternatively, the data from the credentialing database can be provided to a neural network that is trained to generate an examination score from a history of data for the sonography candidate.

Figure 4:
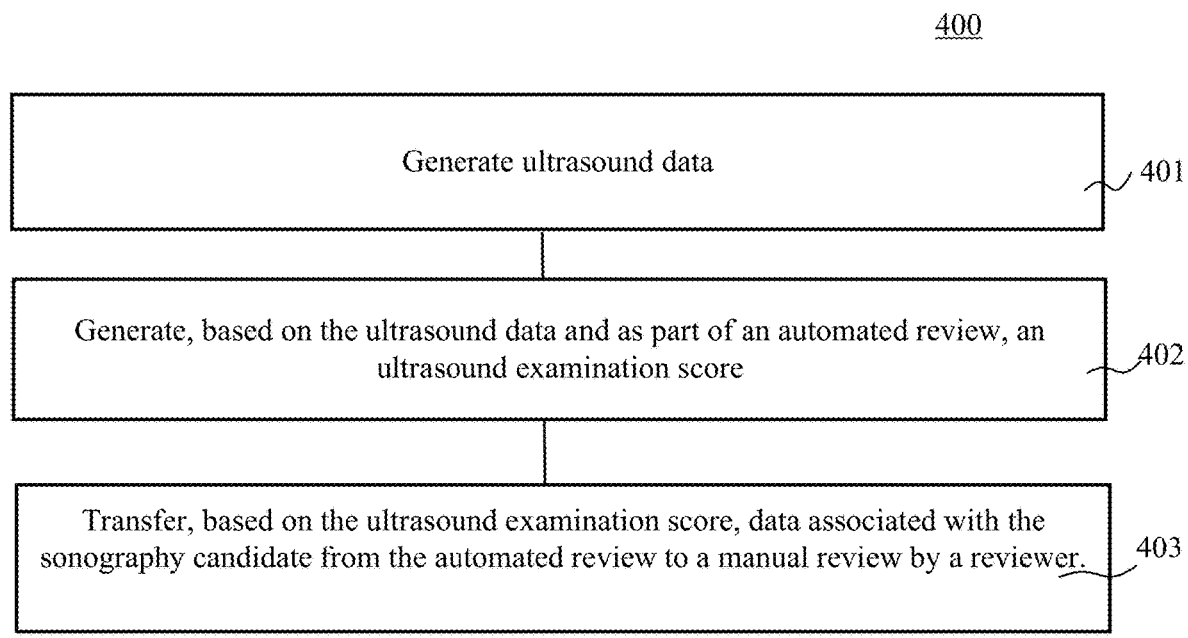
FIG. 4 is a data flow diagram of a process implemented by a credentialing system to issue a sonographer credential to a sonography candidate according to some embodiments.

FIG. 4 is a data flow diagram of a process 400 implemented by a credentialing system to issue a sonographer credential to a sonography candidate according to some embodiments. Referring to FIGS. 1 and 4, a credentialing system includes an ultrasound system that includes a probe 103 coupled to a computing device 102. In some embodiments, the computing device includes one or more processors and a memory coupled to the processor(s) to perform the process 400. In some embodiments, the process 400 is performed using processing logic. The processing logic may comprise hardware (circuitry, dedicated logic, etc.), software (such as is run on a general-purpose computer system or a dedicated machine), firmware, or combinations thereof. At block 401, ultrasound data are generated using the ultrasound probe. At block 402, an ultrasound examination score is generated, based on the ultrasound data and as part of an automated review. In some embodiments, the computing device is configured to implement one or more neural networks 106 to generate an image quality score based on the ultrasound data as part of the automated review, and the ultrasound examination score is based on the image quality score. In some embodiments, the computing device is implemented to determine, based on the ultrasound data, an anatomy. The computing device can then select, from among a plurality of neural networks and based on the anatomy, the neural network.

In some embodiments, the ultrasound probe includes a touch sensitive surface, and a processor is implemented to generate a grip orientation on the touch sensitive surface. The processor can represent the grip orientation as a grip map, as discussed above. The computing device is implemented to generate the ultrasound examination score based on the grip orientation. In some embodiments, the ultrasound probe includes a pressure sensor implemented to generate pressure data indicating an amount of pressure of the ultrasound probe on a patient, and the computing device is implemented to generate the ultrasound examination score based on the pressure data. In some embodiments, the credentialing system includes an audio processor implemented to record audio content, and the computing device is implemented to generate the ultrasound examination score based on the audio content.

In some embodiments, the ultrasound probe includes an inertial measurement unit implemented to generate motion data for the ultrasound probe, and the computing device is implemented to generate the ultrasound examination score based on the motion data. In some embodiments, the credentialing system includes a sensor system implemented to generate motion data for the sonography candidate (e.g., data indicative of how the sonography candidate moves during the examination), and the computing device is implemented to generate the ultrasound examination score based on the motion data. In some embodiments, the sensor system includes a wearable sensor configured to be worn by the sonography candidate. The motion data can be generated based on data sensed by the wearable sensor. In some embodiments, the credentialing system includes a simulator system (e.g., simulator system 108 in FIG. 1). The simulator system can include a dummy patient, and the ultrasound probe can be implemented to transmit ultrasound into the dummy patient and generate the ultrasound data based on reflections of the ultrasound from the dummy patient. As shown in FIG. 4, the computing device transfers, based on the ultrasound examination score, data associated with the sonography candidate from the automated review to a manual review by a reviewer at block 403. By transferring the sonography candidate from an automated review based on neural networks to a manual review based on a reviewer, the computing device advances the sonography candidate through the credentialing process and closer to the goal of issuing a sonography certificate. In some embodiments, the credentialing system anonymizes the data for the candidate when the candidate is transferred from the automated review to the manual review, so that the reviewer cannot identify the candidate. This anonymization can remove inherent bias by the reviewer.

In some embodiments, the credentialing system includes a credentialing database that stores examination results of sonography candidates, as described above. The computing device can transfer the sonography candidate from the automated review to the manual review based on the examination results from the credentialing database for at least some of the sonography candidates that are different from the sonography candidate. In some embodiments, the credentialing system is trained to look at sonography candidates that passed the manual review, and what they have in common with each other, such as what type of examinations in the automated review they passed. The credentialing system can then transfer data associated with the current sonography candidate from the automated review to the manual review only if the current sonography candidate also passed the examinations in the automated review that the other sonography candidates passed. In this way, the credentialing system can use the data of other sonography candidates as a predictor of performance for a current sonography candidate. The data from the credentialing database can be provided to a neural network that is trained to predict the performance of the current sonography candidate. The neural network can be the neural network as illustrated in FIG. 1, or an additional neural network.

In some embodiments, the credentialing system uses the data (e.g., from the credentialing database) of multiple sonography candidates to determine an examination score, such as a grade of a current candidate. For example, the credentialing system can grade "on a curve", such as by looking at multiple examination scores of multiple candidates and assigning a passing grade to the top half of the candidates and a failing grade to the bottom half of the candidates, or a passing grade to the top 30% of the candidates and a failing grade to the bottom 70% of the candidates, according to their examinations scores.

Figure 5:
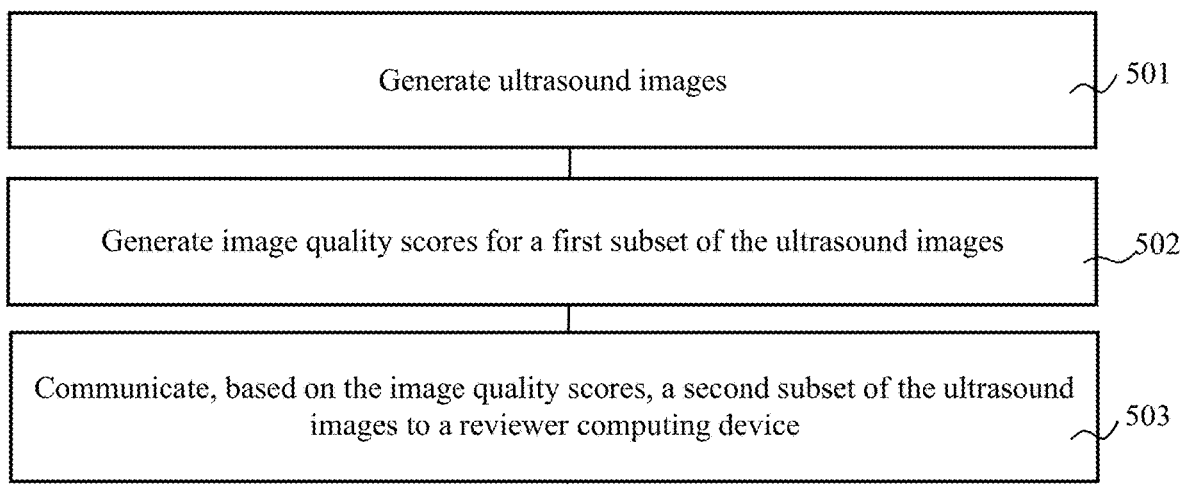
FIG. 5 is a data flow diagram of a process implemented by a credentialing system to issue a sonographer credential to a sonography candidate according to some embodiments.

FIG. 5 is a data flow diagram of a process 500 implemented by a credentialing system to issue a sonographer credential to a sonography candidate according to some embodiments. Referring to FIGS. 1 and 5, a credentialing system includes an ultrasound system 101 configured to generate ultrasound images (block 501). The credentialing system includes a candidate credentialing application 107 implemented at least partially in hardware of the credentialing system and configured to generate image quality scores for a first subset of the ultrasound images (block 502) and communicate, based on the image quality scores, a second subset of the ultrasound images to a reviewer computing device (block 503). For example, the first subset of images can correspond to a first anatomy being imaged (e.g., a bladder), a first ultrasound protocol (e.g., eFAST), a first examination preset (e.g., a bladder preset), etc., and the second subset of images can correspond to a second anatomy being imaged (e.g., a lung), a second protocol (e.g., a protocol other than eFAST), a second examination type (e.g., a cardiac preset), etc.

In some embodiments, the first subset of the ultrasound images and the second subset of the ultrasound images are disjoint with respect to one another. In some embodiments, the credentialing system includes a reviewer computing device 113 coupled to the computing device 102. In some embodiments, the candidate credentialing application determines, based on at least one of the image quality scores being below a threshold score, a guidance for the sonography candidate to improve the at least one of the image quality scores. The credentialing system can include a display device that displays a visual representation of the guidance. In some embodiments, the visual representation incudes at least one of a training video, an icon of an ultrasound probe, an arrow to indicate a direction to move the ultrasound probe, and an icon of a grip orientation for holding the ultrasound probe.

In some embodiments, the candidate credentialing application communicates the second subset of the ultrasound images to the reviewer computing device based at least on a percentage of the image quality scores being above a threshold score. For example, the candidate credentialing application communicates the second subset of the ultrasound images when the percentage of the image quality scores is greater than a threshold score. In some embodiments, the first subset includes at least one ultrasound image of a specified anatomy. In some embodiments, the first subset includes at least one ultrasound image generated with the ultrasound system in a specified imaging mode. In some embodiments, the first subset includes at least one ultrasound image generated according to a specified examination protocol.

In some embodiments, the candidate credentialing application includes a neural network that generates the image quality scores. In some embodiments, the neural network generates the image quality scores based on at least one of a grip orientation of an ultrasound probe of the ultrasound system (e.g., a grip map as described above with regard to FIG. 2), an amount of movement of the ultrasound probe, an amount of movement of the sonography candidate, audio content, an amount of pressure applied by the ultrasound probe to a patient, and an amount of time taken by the sonography candidate to operate the ultrasound system to generate the ultrasound images.

Figure 6:
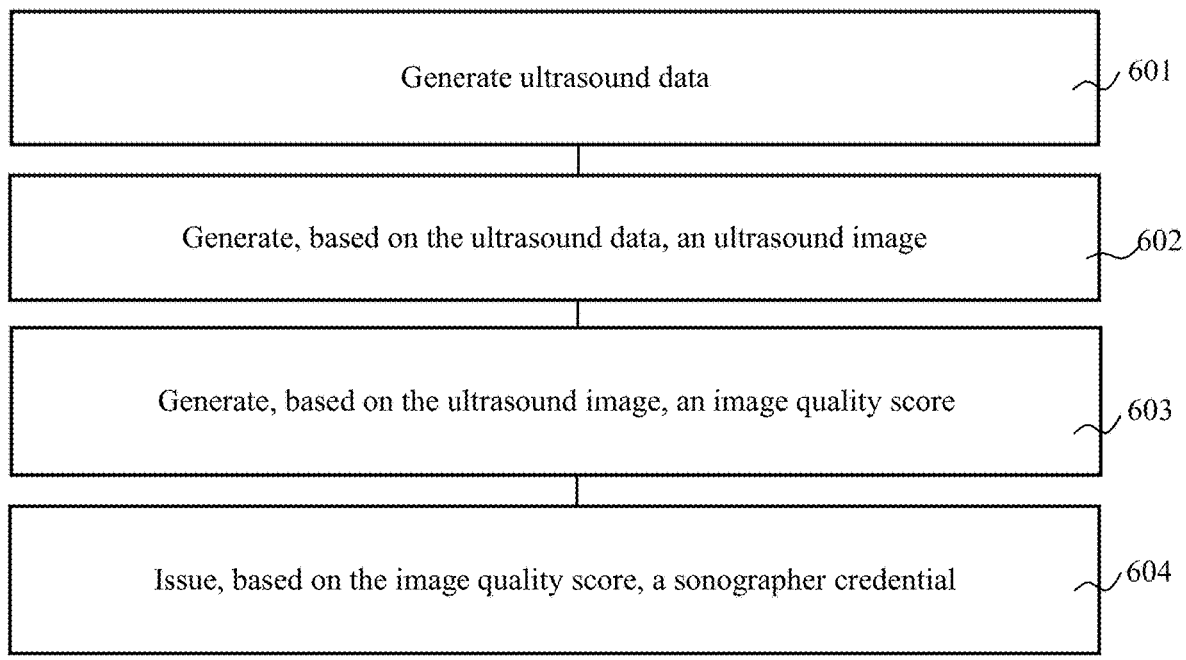
FIG. 6 is a data flow diagram of a process implemented by a sonography credentialing system according to some embodiments.

FIG. 6 is a data flow diagram of a process 600 implemented by a sonography credentialing system according to some embodiments. Referring to FIGS. 1 and 6, the sonography credentialing system includes an ultrasound probe 103 configured to generate ultrasound data (block 601). The sonography credentialing system includes a computing device 102 configured to generate, based on the ultrasound data, an ultrasound image (block 602). The sonography credentialing system includes a neural network 106 implemented at least partially in hardware of the computing device to generate, based on the ultrasound image, an image quality score (block 603). The sonography credentialing system includes a credentialing device (e.g., implemented at least in part by a processor of the computing device) configured to issue, based on the image quality score, a sonographer credential (block 604).

In some embodiments, the sonography credentialing system issues the certificate based on a history of scores of candidate. In some embodiments, the sonography credentialing system issues the certificate when a candidate's score is greater than scores of two thirds of other candidate. In some embodiments, the sonography credentialing system issues the certificate when a candidate in top third of all candidates or other criteria.

In some embodiments, the credentialing system provides guidance to the candidate during the ultrasound examination. For instance, the guidance can include a hint that is displayed by the candidate credentialing application on a user interface of the computing device. The credentialing system can determine the guidance using one or more of the neural networks. For example, a neural network can determine, based on the ultrasound data (e.g., an ultrasound image) that an imaging parameter should be adjusted to improve the quality of the ultrasound image. Examples of imaging parameters include gain, depth, and examination type. The neural network can generate an adjustment for the imaging parameter, and the candidate credentialing application can display on the user interface a message to adjust the imaging parameter according to the recommended adjustment from the neural network.

In some embodiments, the guidance includes an indication for movement of the probe. The credentialing system communicates the guidance via the user interface, e.g., by displaying a directional arrow, broadcasting an audio recommendation "move the probe towards the center of the patient", haptic feedback on the probe, combinations thereof, and the like. In some embodiments, the guidance includes a recommendation for certain training to the candidate. For example, the credentialing system can determine, based on one or more of a neural network output, a type of the ultrasound examination being performed, an anatomy being imaged, an imaging parameter, and the ultrasound data, training materials from a database of training materials to improve the sonography skills of the candidate. The server system can maintain the database of training materials and provide recommended training materials to the candidate credentialing application upon request from the candidate computing device.

In some embodiments, the credentialing system generates and communicates the guidance to the candidate computing system based on a request supplied by the candidate to the credentialing system (e.g., a candidate request). The candidate request can be spoken, typed, gestured, etc. For instance, the candidate may speak "help me, how do I hold the probe?", or gesture with the probe in a specified manner, such as swiping an "X" in the air, to indicate that help is needed. In some embodiments, the credentialing system can generate the guidance for the candidate without an explicit request from the candidate. For example, the credentialing system can determine from the outputs of the neural network(s) in the computing device that the candidate is not passing the ultrasound examination (e.g., a neural network is generating quality metrics that correspond to failing scores). Hence, the credentialing system can communicate the guidance to the candidate to instruct the candidate on the proper use of the ultrasound system. In some embodiments, if the credentialing system communicates guidance to the candidate for current ultrasound data, the credentialing system will not accept the current ultrasound data toward credentialing the candidate. Rather, the credentialing system requires that the candidate generate new ultrasound data without guidance offered for the new ultrasound data, and submit this new ultrasound data for review towards credentialing.

Referring back to FIG. 1, the credentialing system includes a simulator system 108 that is coupled to the computing device operated by the candidate 105. The simulator system 108 includes hardware, software, firmware, or combinations thereof, to emulate an ultrasound examination on a live patient when a live patient is not available. For example, for some types of ultrasound examinations and patient conditions that require urgent care, such as the detection of free fluid, it may not be feasible for a candidate to have access to a live patient with the condition and perform an in-training ultrasound examination for credentialing purposes, since such a condition may be life threatening. Hence, the credentialing system includes the simulator system that can generate image data. For example, the credentialing system can include a dummy patient (e.g., a torso and head, a full-body dummy, etc.) that can be imaged by the ultrasound probe. The dummy patient can include artificial anatomy, and the ultrasound probe and computing device can generate ultrasound images of the artificial anatomy.

In some embodiments, the simulator system generates image data that mimic ultrasound images, but are not derived directly from ultrasound signals transmitted by the ultrasound system. For example, the image data can be generated by the simulator system based on positional and orientation data of the probe, such as a point or area of contact on a dummy patient and data corresponding to six degrees of freedom of the probe. In some embodiments, the simulator system generates the image data based on imaging parameters set by the candidate. The positional data, orientation data, and imaging parameters can be aggregated, e.g., into a vector, and supplied as input to a neural network 106. The neural network can be trained to generate an image that looks like an ultrasound image, and this image can be used by the credentialing system for credentialing the candidate.

In some embodiments, the image generated by the simulator system 108 is reviewed by one or more neural networks of the candidate's computing device 102, as described above as part of the automated review. For example, a neural network can generate a quality metric for the image, or a grade for the image. In some embodiments, the credentialing system determines a quality metric or grade for the image based on ground truth images. For example, the credentialing system can include a database of ground truth images gathered by trained experts for various anatomies and examination types. The credentialing system can compare the image generated by the simulator system to the ground truth image, such as in a mean squared error sense (e.g., on pixels or features extracted from the images) to determine the quality metric or grade for the image. In some embodiments, a neural network receives the ground truth image as a second (or conditional) input, in addition to the image generated by the simulator system, to generate the quality metric or grade for the image generated by the simulator system.

Figure 7:
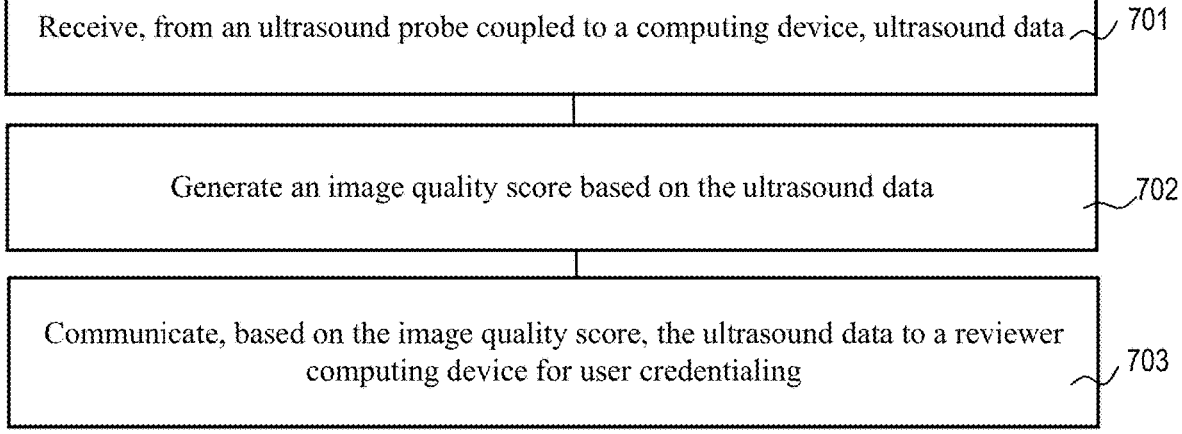
FIG. 7 is a data flow diagram of a method implemented by a computing device according to some embodiments.

FIG. 7 is a data flow diagram of a method 700 implemented by a computing device according to some embodiments, such as the computing device 102 in FIG. 1. The method 700 includes receiving, from an ultrasound probe coupled to the computing device, ultrasound data at block 701. In some embodiments, the ultrasound probe is instructed by the computing device to transmit ultrasound signals into a dummy patient and determine the ultrasound data based on the ultrasound signals. At block 702, an image quality score is generated by the computing device based on the ultrasound data. In some embodiments, the image quality score is generated with a neural network implemented at least partially in hardware of the computing device. In some embodiments, an anatomy is determined based on the ultrasound data and the neural network is selected from among a plurality of neural networks and based on the anatomy. At block 703, the ultrasound data are communicated, based on the image quality score, to a reviewer computing device for user credentialing.

In some embodiments, additional ultrasound data are received from the ultrasound probe and an additional image quality score is generated, by the computing device, based on the additional ultrasound data. In some embodiments, the computing device determines, based on the additional image quality score, not to communicate the additional ultrasound data to the reviewer computing device for the user credentialing. In some embodiments, a guidance to improve the additional image quality score is displayed on a user interface of the computing device. In some embodiments, the guidance includes at least one of an instruction to move the probe, an adjustment to an imaging parameter, and an examination type. In some embodiments, training materials are selected, based on the additional image quality score and the additional ultrasound data. In some embodiments, the training materials are exposed on the computing device for user consumption.

Figure 8:
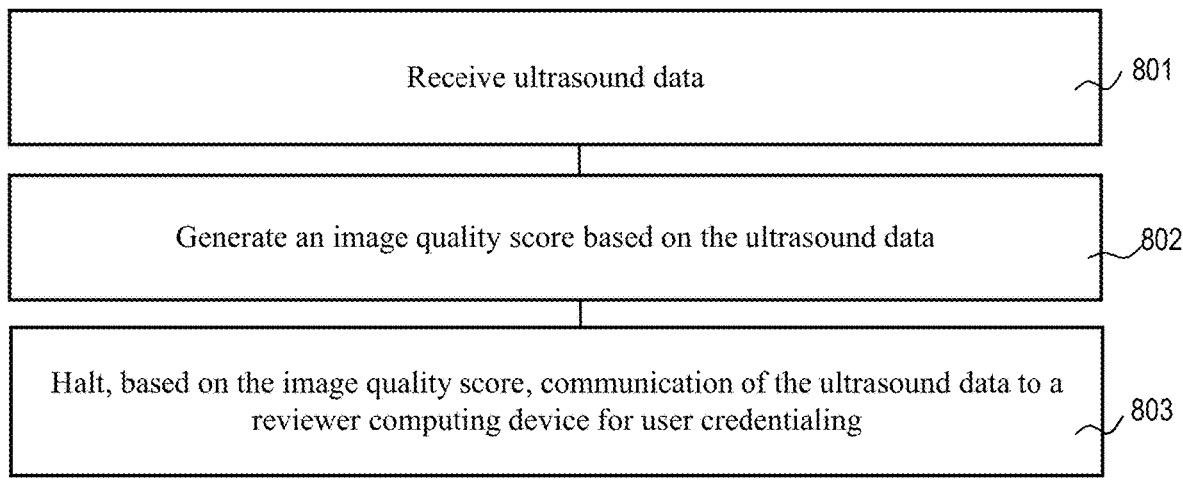
FIG. 8 is a data flow diagram of a method implemented by a computing device according to some embodiments.

FIG. 8 is a data flow diagram of a method 800 implemented by a computing device according to some embodiments, such as the computing device 102 in FIG. 1. The method 800 includes receiving, from an ultrasound probe coupled to the computing device, ultrasound data at block 801. At block 802, an image quality score is generated by the computing device based on the ultrasound data. At block 803, communication of the ultrasound data to a reviewer computing device for user credentialing is halted based on the image quality score. The computing device can halt the communication of the ultrasound data because the image quality score is below a threshold quality score, and therefore the credentialing system determines that the ultrasound data is not "good enough" to have the reviewer spend time grading the ultrasound data as part of the manual review. Hence, the credentialing system is more efficient than conventional credentialing systems that rely solely on manual review and can waste the reviewer's time.

Figure 9:
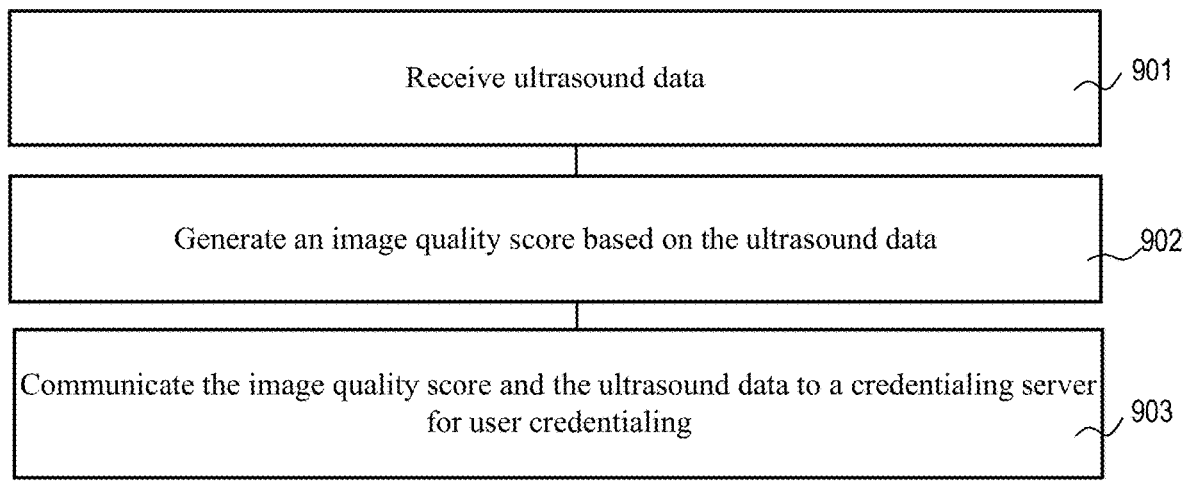
FIG. 9 is a data flow diagram of a method implemented by a computing device according to some embodiments.

FIG. 9 is a data flow diagram of a method 900 implemented by a computing device according to some embodiments, such as the computing device 102 in FIG. 1. The method 900 includes receiving, from an ultrasound probe coupled to the computing device, ultrasound data at block 901. At block 902, an image quality score is generated by the computing device based on the ultrasound data. At block 903, the image quality score and the ultrasound data are communicated to a credentialing server for user credentialing.

Figure 10:
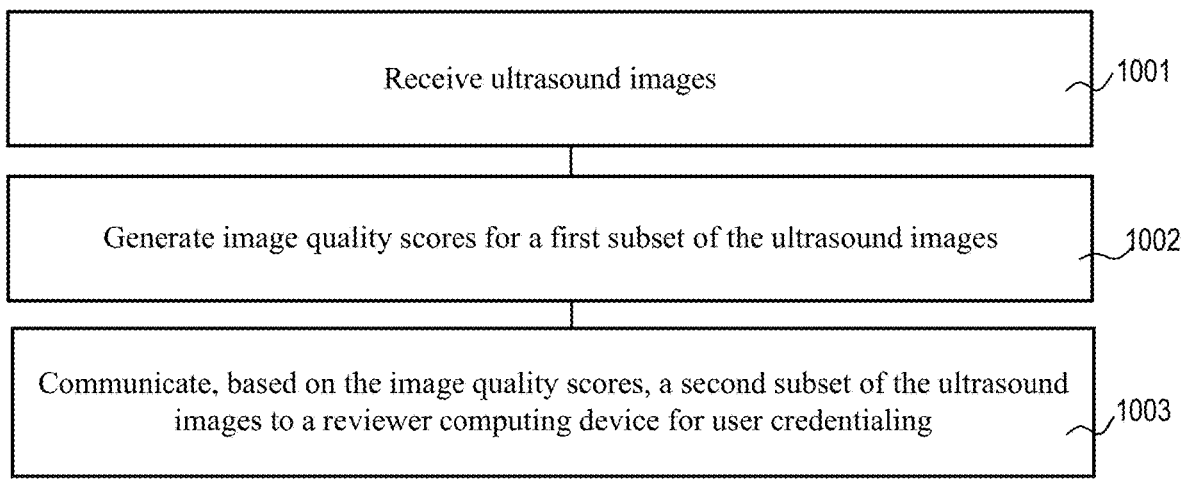
FIG. 10 is a data flow diagram of a method implemented by a computing device according to some embodiments.

FIG. 10 is a data flow diagram of a method 1000 implemented by a computing device according to some embodiments, such as the computing device 102 in FIG. 1. The method 1000 includes receiving ultrasound images at block 1001. At block 1002, image quality scores for a first subset of the ultrasound images are generated. At block 1003, a second subset of the ultrasound images are communicated based on the image quality scores to a reviewer computing device for user credentialing. In some embodiments, the first subset of the ultrasound images and the second subset of the ultrasound images are disjoint with respect to one another. For example, the first subset of images can correspond to a first anatomy being imaged (e.g., a bladder), a first ultrasound protocol (e.g., eFAST), a first examination preset (e.g., a bladder preset), etc., and the second subset of images can correspond to a second anatomy being imaged (e.g., a lung), a second protocol (e.g., a protocol other than eFAST), a second examination type (e.g., a cardiac preset), etc.

In some embodiments, method 1000 includes communicating the first subset of the ultrasound images and the image quality scores to a credentialing server for user credentialing. In some embodiments, method 1000 includes communicating a comment to a candidate computing device that generated the ultrasound images. In some embodiments, the comment indicates the communicating of the second subset to the reviewer computing device. In some embodiments, the comment includes at least one of the image quality scores for the first subset. In some embodiments, the comment indicates that at least one ultrasound image of the first subset has an image quality score corresponding to a failing grade. In some embodiments, method 1000 includes obtaining an image threshold number. In some embodiments, the comment indicates that at least the image threshold number of the ultrasound images of the first subset have an image quality score corresponding to a passing grade.

Figure 11:
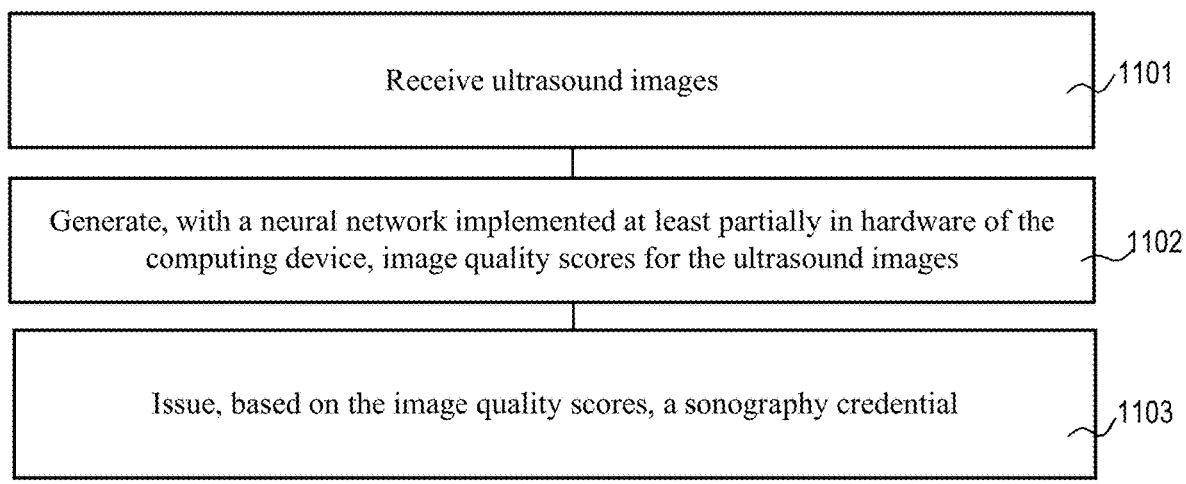
FIG. 11 is a data flow diagram of a method implemented by a computing device according to some embodiments.

FIG. 11 is a data flow diagram of a method 1100 implemented by a computing device according to some embodiments, such as the computing device 102 and/or the reviewer computing device 113 in FIG. 1. The method 1100 includes receiving ultrasound images at block 1101. At block 1102, image quality scores for the ultrasound images are generated using a neural network implemented at least partially in hardware of the computing device. At block 1103, a sonography credential is issued based on the image quality scores.

Figure 12:
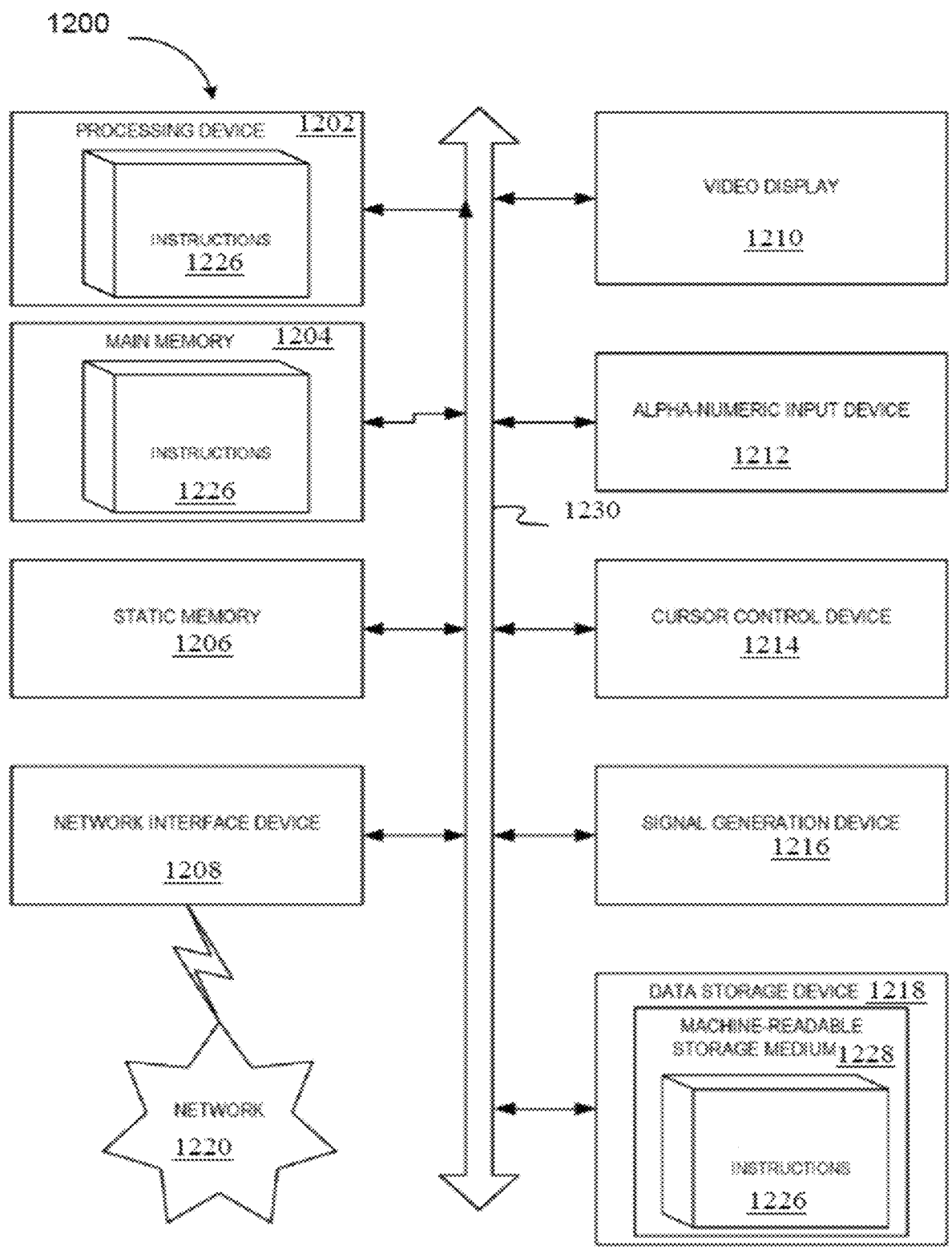
FIG. 12 is a block diagram of an example computing device that can perform one or more of the operations described herein, in accordance with some embodiments.

FIG. 12 is a block diagram of an example computing device 1200 that may perform one or more of the operations described herein, in accordance with some embodiments. Computing device 1200 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 1200 may be one or more of an access point and a packet forwarding component.

The example computing device 1200 may include a processing device (e.g., a general-purpose processor, a PLD, etc.) 1202, a main memory 1204 (e.g., synchronous dynamic random-access memory (DRAM), read-only memory (ROM)), a static memory 1206 (e.g., flash memory and a data storage device 1218), which may communicate with each other via a bus 1230. Processing device 1202 may be provided by one or more general-purpose processing devices such as a microprocessor, central processing unit, or the like. In an illustrative example, processing device 1202 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 1202 may also comprise one or more special-purpose processing devices such as an application specific integrated circuit (ASIC), a field programmable gate array (FPGA), a digital signal processor (DSP), network processor, or the like. The processing device 1202 may be configured to execute the operations described herein, in accordance with one or more aspects of the present disclosure, for performing the operations and steps discussed herein.

Computing device 1200 may further include a network interface device 1208 which may communicate with a network 1220. The computing device 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse) and an acoustic signal generation device 1216 (e.g., a speaker, and/or a microphone). In one embodiment, video display unit 1210, alphanumeric input device 1212, and cursor control device 1214 may be combined into a single component or device (e.g., an LCD touch screen).

Data storage device 1218 may include a computer-readable storage medium 1228 on which may be stored one or more sets of instructions 1226, e.g., instructions for carrying out the operations described herein, in accordance with one or more aspects of the present disclosure. Instructions 1226 may also reside, completely or at least partially, within main memory 1204 and/or within processing device 1202 during execution thereof by computing device 1200, main memory 1204 and processing device 1202 also constituting computer-readable media. The instructions may further be transmitted or received over a network 1220 via network interface device 1208.

While computer-readable storage medium 1228 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

Unless specifically stated otherwise, terms such as "transmitting," "determining," "receiving," "generating," "or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general-purpose computing device selectively programmed by a computer program stored in the computing device. Such a computer program may be stored in a computer-readable non-transitory storage medium.

The methods and illustrative examples described herein are not inherently related to any particular computer or other apparatus. Various general-purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A credentialing system for issuing a sonographer credential to a sonography candidate, the credentialing system comprising:
    an ultrasound probe comprising a grip portion coupled to a computing device and configured to generate ultrasound data and configured to generate grip data indicating an amount of pressure caused by a user grip of the grip portion, wherein the ultrasound probe includes a pressure sensor implemented to generate pressure data indicating an amount of pressure of the ultrasound probe on a patient, and wherein the grip data is a grip map indicating amounts of pressure applied at a plurality of locations on the grip portion by the sonography candidate; and
    the computing device configured to:
        generate, based on the ultrasound data and the amount of pressure caused by the user grip and the pressure data and as part of an automated review, an ultrasound examination score; and
        transfer, based on the ultrasound examination score, the sonography candidate from the automated review to a manual review by a reviewer.

2. The credentialing system as described in claim 1, wherein the computing device is configured to implement a neural network to generate an image quality score based on the ultrasound data as part of the automated review, and the ultrasound examination score is based on the image quality score.

3. The credentialing system as described in claim 2, wherein the computing device is implemented to:
    determine, based on the ultrasound data, an anatomy; and
    select, from among a plurality of neural networks and based on the anatomy, the neural network.

4. The credentialing system as described in claim 1, wherein the grip portion includes a touch sensitive surface, and wherein the ultrasound probe further comprises a processor implemented to generate a grip orientation on the touch sensitive surface, wherein the computing device is implemented to generate the ultrasound examination score based on the grip orientation.

5. The credentialing system as described in claim 1, further comprising an audio processor implemented to record audio content, wherein the computing device is implemented to generate the ultrasound examination score based on the audio content.

6. The credentialing system as described in claim 1, wherein the ultrasound probe includes an inertial measurement unit implemented to generate motion data for the ultrasound probe, and wherein the computing device is implemented to generate the ultrasound examination score based on the motion data.

7. The credentialing system as described in claim 1, further comprising a sensor system implemented to generate motion data for the sonography candidate, wherein the computing device is implemented to generate the ultrasound examination score based on the motion data.

8. The credentialing system as described in claim 7, wherein the sensor system includes a wearable sensor configured to be worn by the sonography candidate.

9. The credentialing system as described in claim 1, further comprising a simulator system including a dummy patient, wherein the ultrasound probe is implemented to transmit ultrasound into the dummy patient and generate the ultrasound data based on reflections of the ultrasound from the dummy patient.

10. The credentialing system as described in claim 1, further comprising a credentialing database implemented to store examination results of sonography candidates, wherein the computing device is implemented to transfer the sonography candidate from the automated review to the manual review based on the examination results from the credentialing database for at least some of the sonography candidates that are different from the sonography candidate.

11. The credentialing system as described in claim 1, wherein the computing device is configured to implement a neural network including a first input to receive one or more ultrasound images and one or more second inputs to receive additional data including the grip data and an output coupled to the first input and the second input to generate the ultrasound examination score.

12. The credentialing system as described in claim 11, wherein the additional data further include one or more of candidate motion data, audio data, probe orientation data, pressure data, or temporal data.

13. The credentialing system as described in claim 11, wherein the neural network includes a plurality of neural networks.

14. The credentialing system as described in claim 1, further comprising:
a camera coupled to the computing device to determine a location of the ultrasound probe.

15. A computer implemented method to issue a sonographer credential to a sonography candidate, the method comprising:
generating, by an ultrasound probe ultrasound data, the ultrasound probe comprising a grip portion, wherein the ultrasound probe includes a pressure sensor implemented to generate pressure data indicating an amount of pressure of the ultrasound probe on a patient;
generating, by a processor, grip data indicating an amount of pressure caused by a user grip of the grip portion of the ultrasound probe, wherein the grip data is a grip map indicating amounts of pressure applied at a plurality of locations on the grip portion by the sonography candidate; and
generating, by the processor, an ultrasound examination score as part of an automated review based on the ultrasound data and the amount of pressure caused by the user grip and the pressure data; and
transferring, based on the ultrasound examination score, the sonography candidate from the automated review to a manual review by a reviewer.

16. The computer implemented method as described in claim 15, wherein the ultrasound examination score is generated as part of an automated review using a neural network including a first input to receive one or more ultrasound images and one or more second inputs to receive additional data including the grip data and an output coupled to the first input and the second input to generate the ultrasound examination score, wherein the neural network is used to generate an image quality score based on the ultrasound data and the grip data as part of the automated review, and the ultrasound examination score is based on the image quality score.

17. The computer implemented method as described in claim 15, further comprising:
determining, based on the ultrasound data, an anatomy; and
selecting, from among a plurality of neural networks and based on the anatomy, the neural network.

18. The computer implemented method as described in claim 15, wherein the additional data further include one or more of candidate motion data, audio data, probe orientation data, pressure data, or temporal data.

* * * * *